US012648809B2

(12) United States Patent
Wang et al.

(10) Patent No.: US 12,648,809 B2
(45) Date of Patent: Jun. 9, 2026

(54) ABLATION DEVICE AND ABLATION SYSTEM

(71) Applicant: HANGZHOU DINOVA EP TECHNOLOGY CO., LTD, Zhejiang (CN)

(72) Inventors: Yongsheng Wang, Hangzhou (CN); Cheng Liu, Hangzhou (CN); Kun Wang, Hangzhou (CN); Jie Chen, Hangzhou (CN); Yan You, Zhejiang (CN)

(73) Assignee: Hangzhou Dinova EP Technology Co., Ltd., Hangzhou (CN)

( * ) Notice: Subject to any disclaimer, the term of this patent is extended or adjusted under 35 U.S.C. 154(b) by 629 days.

(21) Appl. No.: 18/088,600

(22) Filed: Dec. 25, 2022

(65) Prior Publication Data

US 2023/0130692 A1     Apr. 27, 2023

Related U.S. Application Data

(63) Continuation of application No. PCT/CN2021/102578, filed on Jun. 26, 2021.

(30) Foreign Application Priority Data

Jun. 28, 2020    (CN) ......................... 202010601824.X
Jun. 28, 2020    (CN) .......................... 202021222040.8

(51) Int. Cl.
    *A61B 18/14*        (2006.01)
    *A61B 18/00*        (2006.01)
(52) U.S. Cl.
    CPC .. *A61B 18/1492* (2013.01); *A61B 2018/0016* (2013.01); *A61B 2018/00267* (2013.01); *A61B 2018/00577* (2013.01)

(58) Field of Classification Search
    CPC ........ A61B 18/1492; A61B 2018/0016; A61B 2018/00267; A61B 2018/00577
    (Continued)

(56) References Cited

U.S. PATENT DOCUMENTS

2002/0177765 A1    11/2002    Bowe et al.
2009/0216221 A1    8/2009    Davis et al.
    (Continued)

FOREIGN PATENT DOCUMENTS

CN        105796090 A      7/2016
CN        106102628 A     11/2016
    (Continued)

OTHER PUBLICATIONS

Extended European Search Report Dated Jun. 24, 2024 for Corresponding European Application No. 21833859.8.
    (Continued)

*Primary Examiner* — Beverly M Flanagan

(57)    ABSTRACT

An ablation device and an ablation system provided with an ablation device, include an ablation assembly and an adjustment assembly provided at the proximal end of the ablation assembly. The adjustment assembly includes an outer catheter and an inner catheter which extend axially. The ablation assembly includes a supporting framework and an ablation member provided on the supporting framework. The supporting framework includes a positioning frame and a bearing frame. The positioning frame is provided at the distal end relative to the bearing frame, the distal end of the outer catheter is connected to the proximal end of the bearing frame, the distal end of the inner catheter is connected to the distal end of the positioning frame. During moving of the inner catheter relative to the outer catheter, the supporting framework deforms, and the deformation ratio of the positioning frame is less than that of the bearing frame.

20 Claims, 16 Drawing Sheets

(58) Field of Classification Search
USPC ........................................................ 606/41
See application file for complete search history.

(56) References Cited

U.S. PATENT DOCUMENTS

| | | | |
|---|---|---|---|
| 2012/0101413 A1 | 4/2012 | Beetel et al. | |
| 2015/0105772 A1* | 4/2015 | Hill ................... | A61B 18/1492 |
| | | | 606/41 |
| 2021/0161582 A1* | 6/2021 | Byrd ................. | A61B 18/1206 |

FOREIGN PATENT DOCUMENTS

| | | | | |
|---|---|---|---|---|
| CN | 108618841 A | 10/2018 | | |
| CN | 209404936 U | 9/2019 | | |
| CN | 111166462 A | 5/2020 | | |
| EP | 3123972 A1 | 2/2017 | | |
| EP | 3178385 A1 | 6/2017 | | |
| EP | 3300660 A1 | 4/2018 | | |
| EP | 3345540 A1 | 7/2018 | | |
| WO | WO 2008141150 A2 | 11/2008 | | |
| WO | WO-2014066383 A1 * | 5/2014 | ......... | A61B 17/3403 |
| WO | 2021/126980 A1 | 6/2021 | | |

OTHER PUBLICATIONS

International Search Report dated Sep. 28, 2021 for corresponding PCT Application No. PCT/CN2021/102578.
Written Opinion of the International Search Authority in corresponding International application No. PCT/CN2021/102578.

* cited by examiner

ABLATION DEVICE AND ABLATION SYSTEM

This application claims priority of International Patent Application No. PCT/CN2021/102578, filed Jun. 26, 2021, which claims priorities to Chinese Patent Application Nos. 202021222040.8 and 202010601824.X, both filed on Jun. 28, 2020, the entire contents of which are hereby incorporated by reference.

TECHNICAL FIELD

The present application relates to the technical field of interventional medical devices, and particularly relates to an ablation device and an ablation system including the ablation device.

BACKGROUND

Atrial fibrillation (AF) is the most common persistent arrhythmia. With the increase of age, the incidence of atrial fibrillation is increasing, reaching 10% in people over 75 years old. The frequency of atrial activation during atrial fibrillation is 300-600 beats/min, and the heartbeat frequency is generally fast and irregular, sometimes reaching 100-160 beats/min, which is not only much faster than that of normal people, but also absolutely irregular, the atria lose effective contractile function. Atrial fibrillation generally increases the risk of many potentially fatal complications. Including thromboembolic stroke, dilated cardiomyopathy and congestive heart failure. Common atrial fibrillation symptoms such as palpitation, chest pain, dyspnea, fatigue and dizziness can also affect the quality of life. Compared with normal people, the average incidence of atrial fibrillation increased fivefold and the mortality rate tripled.

Tissue ablation is commonly used to treat various arrhythmias, including atrial fibrillation. In order to treat arrhythmias, ablation may be performed using an ablation catheter to alter the tissue, for example to prevent abnormal electrical propagation and/or to disrupt abnormal electrical conduction through the cardiac tissue. Ablation treatment includes many aspects: on the one hand, it is thermal ablation, such as radiofrequency ablation, laser ablation, microwave ablation, thermal substance ablation, and so on; on the other hand, it is pulse ablation using the principle of biological electroporation.

When using ablation catheter to ablate the pulmonary vein, the ablation catheter slides along the atrial wall. In fact, it is difficult to position the distal ablation catheter around the orifice of the pulmonary vein and point to the center of the pulmonary vein. Even if the electrophysiologist is able to direct the ablation catheter to the ostium, the periodic blood flow through the pulmonary vein may also force the ablation catheter to be away from the atrial wall because the distal end of the ablation catheter does not have any supporting point in the atria, which makes the distal end of the ablation catheter unable to be positioned at the orifice of the pulmonary vein, and the ablation catheter after entering the pulmonary vein unable to form at least one full circle of ablation region.

SUMMARY

An object of the present disclosure is to provide an ablation device that is relatively easy to be positioned at the orifice of the pulmonary vein during pulmonary vein ablation, so as to ensure that the ablation device can form at least one full circle of ablation region after entering the pulmonary vein.

In order to solve the above technical problem, the present disclosure provides an ablation device, which includes an ablation assembly and an adjustment assembly provided at the proximal end of the ablation assembly. The adjustment assembly includes an outer catheter and an inner catheter which both extend in an axial direction. The ablation assembly includes a supporting framework and an ablation member provided on the supporting framework. The supporting framework includes a positioning frame and a bearing frame. The positioning frame is provided at the distal end relative to the bearing frame. The distal end of the outer catheter is connected to the proximal end of the bearing frame, and the distal end of the inner catheter is connected to the distal end of the positioning frame. During moving of the inner catheter relative to the outer catheter, the supporting framework deforms, and the deformation ratio of the positioning frame is less than the deformation ratio of the bearing frame.

The present disclosure further provides an ablation system, which includes a mapping device and the ablation device. The inner catheter is hollow and tubular. The mapping device includes a mapping catheter and a mapping electrode provided at the distal end of the mapping catheter. The mapping catheter is inserted into the inner catheter, and the mapping electrode extends out from the distal end of the inner catheter to contact a tissue wall to detect electrophysiological signals in the target tissue region.

The supporting framework of the ablation device of the present disclosure includes the positioning frame and bearing frame, the positioning frame is provided at the distal end relative to the bearing frame, the distal end of the outer catheter is connected to the proximal end of the bearing frame, and the distal end of the inner catheter is connected to the distal end of the positioning frame. During moving of the inner catheter relative to the outer catheter, the supporting framework deforms, and the deformation ratio of the positioning frame is less than the deformation ratio of the bearing frame. Thus, the bearing frame is easy to change its radial sire during the deformation thereof to close to the target tissue region; and, compared with the bearing frame, the positioning frame is easier to maintain its original shape since the deformation ratio thereof is smaller. The positioning frame is located at the distal end of the ablation device, configured for positioning in the pulmonary vein. That is, the positioning frame is inserted into the orifice of the pulmonary vein, so as to ensure a better centering effect of the ablation device, which is beneficial to form a full circle of ablation region around the orifice of the pulmonary vein. The problem of large deformation of the positioning frame during adjusting the diameter of the bearing frame and failure to abut against the inner wall of the pulmonary vein, which causes the ablation assembly to be unable to align around the orifice of the pulmonary vein and produce discontinuous ablation regions, is avoided to generate.

BRIEF DESCRIPTION OF THE DRAWINGS

In order to illustrate the technical solutions according to the embodiments of the present application more clearly, the drawings needed to be used in the embodiments will be described briefly below. Apparently, the drawings in the following description show some embodiments of the present application. For persons of ordinary skill in the art, other drawings can be obtained based on these drawings without creative efforts.

DESCRIPTION OF THE EMBODIMENTS

Figure 1:
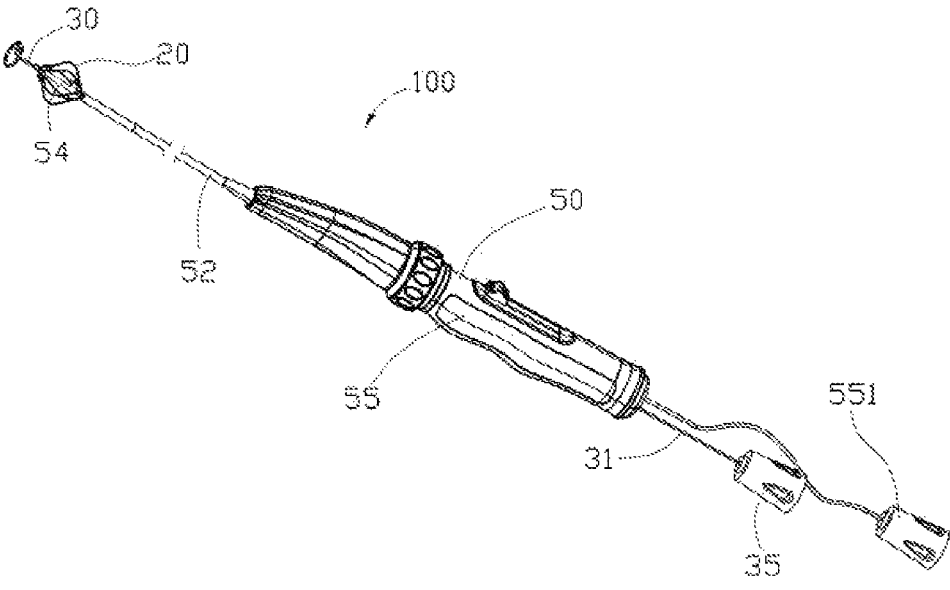
FIG. 1 is a schematic view of an ablation system according to a first embodiment of the present application.
Figure 2:
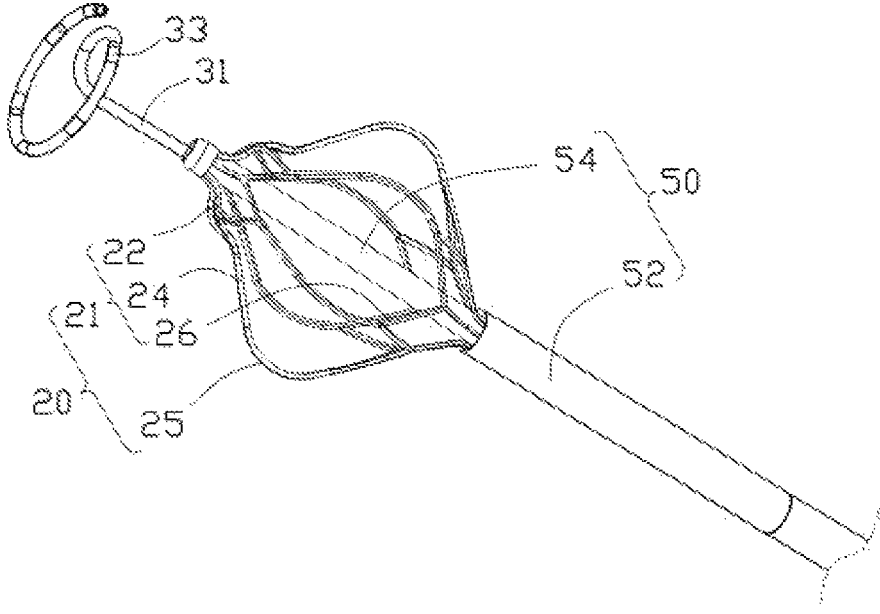
FIG. 2 is a schematic, enlarged view of an ablation assembly, a mapping device and portions of outer and inner catheters of FIG. 1.

The technical solutions according to the embodiments of the present application will be clearly and completely described with reference to drawings in the embodiments of the present application. Apparently, the embodiments described are merely some embodiments, but not all of the embodiments of the present application. All other embodiments obtained by persons of ordinary skill in the art based on the embodiments of the present application without creative efforts shall fall within the protection scope of the present application.

In the description of this application, the "proximal end" means an end close to the operator during the surgical procedure, and the "distal end" means an end remote from the operator during the surgical procedure. The axial direction means a direction in which the central axis of the device is located, and the radial direction is a direction perpendicular to the central axis. Such definition is only for convenience of description and is not to be considered as a limitation of the present application. "Connection of part A and part B" means that part A is directly connected to part B, or part A is indirectly connected to part 8 by other parts.

Referring to FIGS. 1-5, the present application provides an ablation system, which includes an ablation device 100 and a mapping device 30. The ablation device 100 includes an ablation assembly 20 and an adjustment assembly 50 provided at the proximal end of the ablation assembly 20. The adjustment assembly 50 includes an outer catheter 52, an inner catheter 54 and a handle 55, all extending axially.

The ablation assembly 20 includes a supporting framework 21 and an ablation member 25 provided on the supporting framework 21. The supporting framework 21 includes a positioning frame 22 and a bearing frame 24. The positioning frame 22 is provided at the distal end relative to the bearing frame 24. The distal end of the outer catheter 52 is connected to the proximal end of the bearing frame 24, the distal end of the inner catheter 54 is connected to the distal end of the positioning frame 22, and the proximal end of the positioning frame 22 is connected to the distal end of the bearing frame 24. During axial movement of the inner catheter 54 relative to the outer catheter 52, the supporting framework 21 deforms, and the deformation ratio of the positioning frame 22 is less than the deformation ratio of the bearing frame 24.

The deformation ratio is a ratio of the size of the frame in the completely released state minus the size after deformation to the size in the completely released state. For example, in the axial direction, if the size of the frame in the completely released state is L1, the size of the frame after deformation is L2, and the deformation ratio is denoted as A, that is $A=(L1-L2)/L1$.

Specifically, in the axial direction, if the size of the positioning frame 22 in the completely released state is M1, the size of the positioning frame 22 after deformation is M2, and the deformation ratio is denoted as A1, that is $A1=(M1-M2)/M1$.

Specifically, in the axial direction, if the size of the bearing frame 24 in the completely released state is N1, the size of the bearing frame 24 after deformation is N2, and the deformation ratio is denoted as A2, that is $A2=(N1-N2)/N1$.

The deformation ratio of the positioning frame 22 is less than the deformation ratio of the bearing frame 24, that is $A1<A2$.

In this embodiment, in the completely released state of the supporting framework 21, the positioning frame 22 and the bearing frame 24 both are frame structures with inner cavities, and the radial and axial sizes of the positioning frame 22 both are less than the radial and axial sizes of the bearing frame 24. In a modified embodiment, the radial and/or axial sizes of the positioning frame 22 are greater than or equal to the radial and axial sizes of the bearing frame 24.

The supporting framework 21 is at least one of a mesh structure, a rod structure, or a frame structure. The supporting framework 21 may be formed by cutting an elastic metal pipe, or may be formed by weaving elastic metal filaments, or may be processed in a manner of partial weaving combined with partial pipe cutting, different parts may be fixed to each other by welding or by connectors. The material of the pipe is metal or non-metal material, preferably memory metal material, preferably nickel-titanium alloy material. In this embodiment, the supporting framework 21 is formed by cutting and shaping a piece of nickel-titanium alloy pipe, and a cross section of the cutting pipe forming the positioning frame 22 is the same as a cross section of the cutting pipe forming the bearing frame 24. When the inner catheter 54 moves relative to the outer catheter 52, the deformation ratio of the cutting pipe of the positioning frame 22 is less than the deformation ratio of the bearing frame 24.

Specifically, during deformation of the supporting framework 21, deformation ratios of the positioning frame 22 in the axial and radial directions are both less than deformation ratios of the bearing frame 24 in the axial and radial directions.

Figure 3:
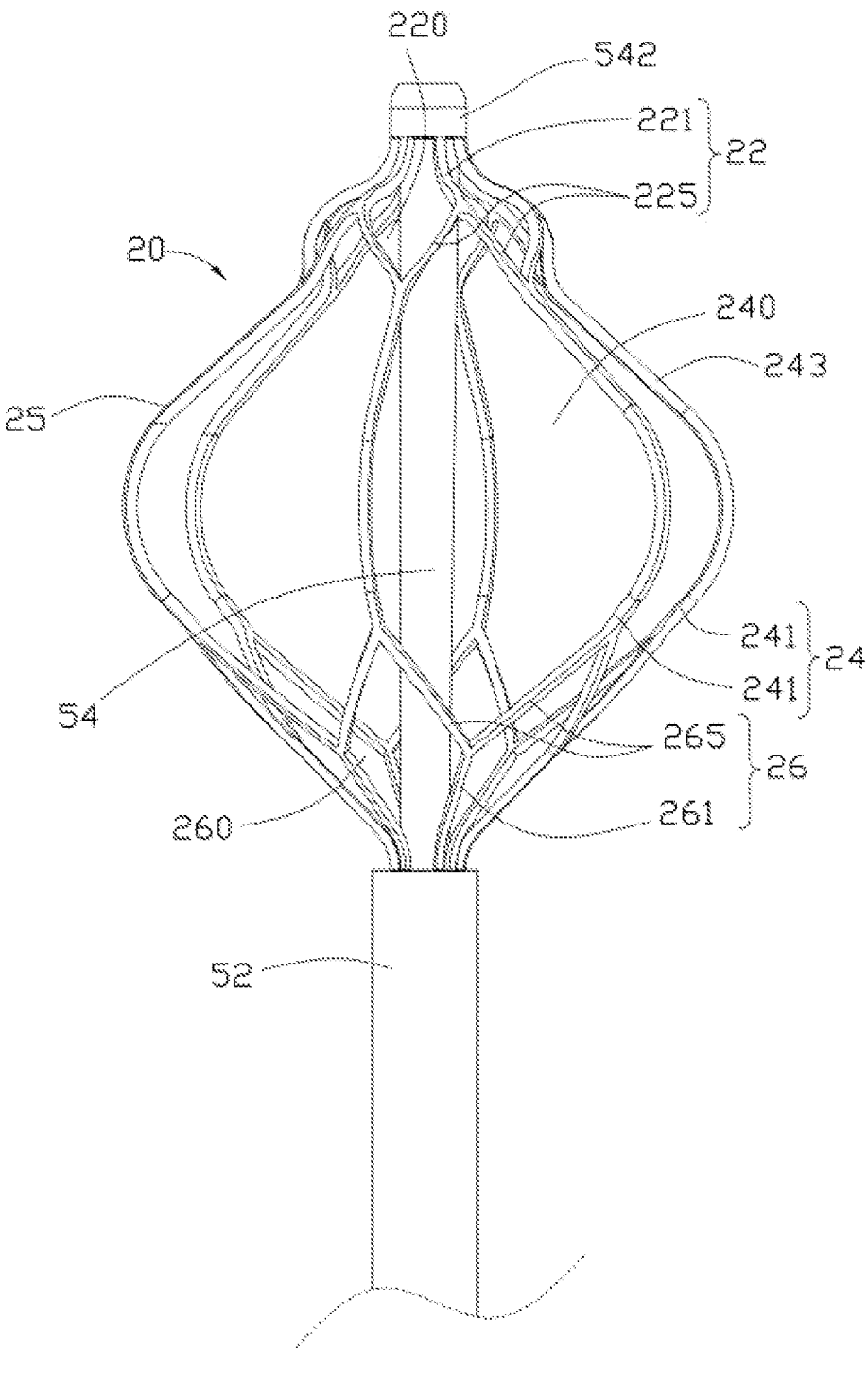
FIG. 3 is a partial, enlarged view of an ablation device of FIG. 1.
Figure 4:
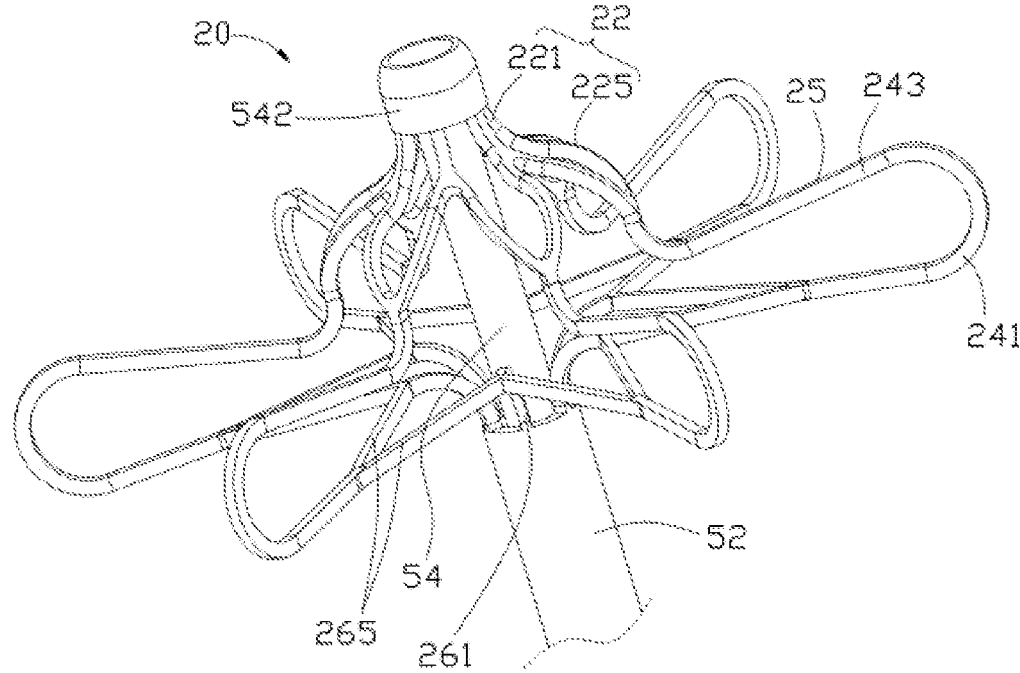
FIG. 4 is a schematic view of the ablation assembly of FIG. 3 in one of its use states.
Figure 5:
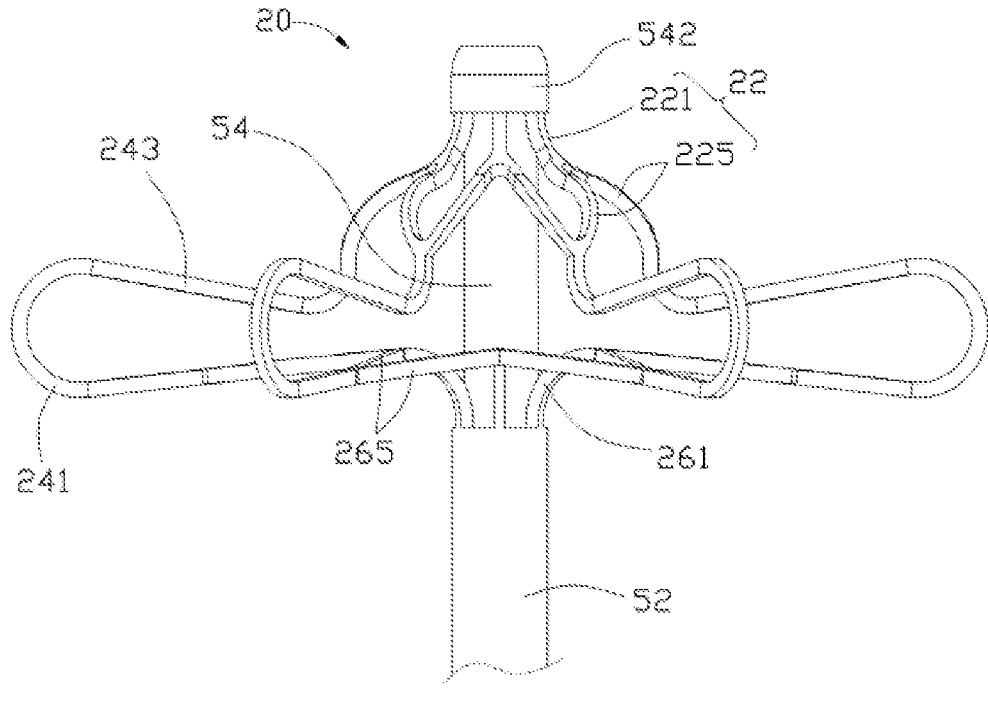
FIG. 5 is a side view of the ablation assembly of FIG. 4.

Optionally, as shown in FIGS. 3-5, the positioning frame 22 and the bearing frame 24 are both mesh structures, the positioning frame 22 is provided with mesh holes 220, and the bearing frame 24 is provided with mesh holes 240. An opening area of the mesh holes 220 of the positioning frame 22 is less than an opening area of the mesh holes 240 of the bearing frame 24, and adjacent mesh filaments of the mesh of the positioning frame 22 are connected to each other, making the positioning frame 24 is not easy to deform. In this embodiment, since the cross section of the cutting pipe of the positioning frame 22 is the same as the cross section of the cutting pipe of the bearing frame 24, and the size of the mesh hole 220 is less than that of the mesh hole 240 (for example, in this embodiment, the mesh hole 220 and mesh hole 240 are both elongated, and, in the completely released state, the opening area of the mesh hole 220 is less than the opening area of the mesh hole 240), and the mesh of the bearing frame 24 is larger than that of the positioning frame 22, the bearing frame 24 is more easily to deform than the positioning frame 22 during relative movement of the outer catheter 52 and the inner catheter 54, so as to close to the target tissue region. The mesh hole 220 of the positioning frame 22 is smaller and the mesh filaments of the positioning frame 22 are connected to and bound with each other, making the positioning frame 22 have a smaller deformation ratio and be easier to maintain its original shape compared with the bearing frame 24, thereby being capable of maintaining a better centering effect. That is, when the ablation assembly 20 is positioned at the orifice of the pulmonary vein, its axis is easier to align with the center of the pulmonary vein. The problem of large deformation of the positioning frame 22 during adjusting the diameter of the bearing frame 24 and failure to abut against the inner walls of the pulmonary vein, which causes the ablation assembly 20 unable to align around the orifice of the pulmonary vein, is avoided to generate. In addition, since the deformation ratio of the contour of the positioning frame 22 is slightly, and the positioning frame 22 extends beyond the bearing frame 24 in the axial direction, it is convenient for the ablation assembly 20 to enter the pulmonary vein, so as to position the bearing frame 24 around the orifice of the pulmonary vein.

In other embodiments, that cross section of the cutting pipe forming the positioning frame 22 is larger than the cross section of the cutting pipe forming the bearing frame 24. In other words, compared with the bearing frame 24, a cross section of a single bar of the positioning frame 22 is greater in size at least in some direction. That is, compared with the bearing frame 24, the diameter of a single bar of the positioning frame 22 is thicker, and the opening area of the mesh holes of the positioning frame 22 is not greater than the opening area of the mesh holes of the bearing frame 24, which makes the deformation ratio of the positioning frame 22 be less than the deformation ratio of the bearing frame 24 during the deformation of the supporting framework 21.

In other embodiments, the rigidity of the cutting pipe of the positioning frame 22 is greater than or equal to the rigidity of the cutting pipe of the bearing frame 24, so that the positioning frame 22 is not easy to generate elastic deformation compared with the bearing frame 24 during the deformation of the supporting framework 21.

In other embodiments, the positioning frame 22 and the bearing frame 24 are formed and enclosed by material filaments. The diameter of the material filaments of the positioning frame 22 is greater than or equal to the diameter of the material filaments of the bearing frame 24, and the opening area of the mesh holes of the positioning frame 22 is less than or equal to the opening area of the mesh holes of the bearing frame 24, so that the deformation ratio of the positioning frame 22 is less than the deformation ratio of the bearing frame 24 during the deformation of the supporting framework 21.

Further, the rigidity of the material filaments of the positioning frame 22 is greater than or equal to the rigidity of the material filaments of the bearing frame 24, so that the deformation ratio of the positioning frame 22 is less than the deformation ratio of the bearing frame 24 during deformation of the supporting framework 21.

It can be understood that, in the embodiments that the deformation ratio of the positioning frame 22 is made to be less than the deformation ratio of the bearing frame 24 during the deformation of the supporting framework 21 by means of changing the cross section of the cutting pipe, the rigidity of the cutting pipe, the diameter of the material filaments, or the rigidity of the material filaments, the opening area of the mesh holes of the positioning frame 22 is less than or equal to the opening area of the mesh holes of the bearing frame 24; or, the opening area of the mesh holes of the positioning frame 22 is greater than the opening area of the mesh holes of the bearing frame 24. That is, the relative size of the opening area of the mesh holes of the positioning frame 22 and the opening area of the mesh holes of the bearing frame 24 is not limited.

Optionally, both the outer catheter 52 and the inner catheter 54 are hollow and tubular, and the inner catheter 54 is disposed in the outer catheter 52. That is, the inner catheter 54 is movably inserted in the inner cavity of the outer catheter 52. When the inner catheter 54 moves axially relative to the outer catheter 54, the axial and radial sizes of the supporting framework 21 are changed. Specifically, during the axial movement of the inner catheter 54 towards the proximal end relative to the outer catheter 52, the axial size of the bearing frame 24 decreases and the radial size of the bearing frame 24 increases; while during the axial movement of the inner catheter 54 towards the distal end relative to the outer catheter 52, the axial size of the bearing frame 24 increases and the radial size of the bearing frame 24 decreases.

In other embodiments, the inner catheter 54 may be rotatable relative to the outer catheter 52 to make the material filaments or cutting pipe of the bearing frame 24 to deform into a spiral shape.

As shown in FIG. 3, the positioning frame 22 includes a plurality of first main bars 221 and a plurality of first branch bars 225. The plurality of first main bars 221 are arranged along the circumferential direction of the inner catheter 54. The distal end of each first main bar 221 is connected to the inner catheter 54, and the proximal end of each first main bar 221 is connected to multiple corresponding first branch bars 225. The bearing frame 24 includes a plurality of bearing bars 241, and the plurality of bearing bars 241 are arranged along the circumferential direction of the inner catheter 54. The distal end of each bearing bar 241 is connected to multiple corresponding first branch bars 225, and the other ends of the multiple first branch bars 225 connected to the same bearing bar 241 are connected to different first main bars 221.

The positioning frame 22 has a mesh shape and is provided at the distal end of the bearing frame 24, and the bearing frame 24 also has a mesh shape and is provided at the proximal end of the positioning frame 22. The positioning frame 22 is configured to be inserted into the pulmonary vein during ablation, and has guiding and positioning functions, so that the bearing frame 24 can form a closed circular ablation region at the orifice of the pulmonary vein. Improving the accuracy of ablation and the success rate of surgery.

In this embodiment, the positioning frame 22 and the bearing frame 24 are integrally cut and shaped by nickel-titanium pipes. The positioning frame 22 includes six first main bars 221 and two first branch bars 225 connected to the proximal end of each first main bar 221. The plurality of first main bars 221 are arranged along the circumferential direction of the inner catheter 54. Preferably, these first main bars 221 are evenly arranged in the circumferential direction of the inner catheter 54. The bearing frame 24 includes six bearing bars 241, which are arranged in the circumferential direction of the inner catheter 54. Preferably, the bearing bars 241 are evenly arranged in the circumferential direction of the inner catheter 54. The distal end of each first main bar 221 is connected to the distal end of the inner catheter 54, and the bearing bar 241 is connected to the first main bar 221 through the first branch bar 225. Specifically, the proximal end of each main bar 221 is connected with two first branch bars 225, the distal end of each bearing bar 241 is connected with two first branch bars 225, and the distal ends of the two first branch bars 225 connected to the distal end of each bearing bar 241 are connected to different first main bars 221, respectively in the completely released state of the supporting framework 21, the radial size of a frame enclosed by the plurality of first main bars 221 and first branch bars 225 is less than the radial size of a frame enclosed by the plurality of bearing bars 241. The bearing bar 241 is provided with an ablation member 25. Specifically, the ablation member 25 is an ablation electrode. At least one of the bearing bars 241 of the bearing frame 24 is provided with the ablation electrode. Specifically, it may be that one of the bearing bars 241 of the bearing frame 24 is provided with the ablation electrode; or, it also may be that each bearing bar 241 is provided with the ablation electrode; or, it also may be that several spaced bearing bars 241 or several adjacent bearing bars 241 are provided with the ablation electrodes. When the ablation device 100 is in use, the ablation member 25 on the bearing bar 241 is configured to perform circular ablation, such as perform circular ablation at the orifice of the pulmonary vein. The inner catheter 54 of the adjustment assembly 50 is movably inserted into the outer catheter 52, and the distal end of the inner catheter 54 is capable of extending out from the distal opening of the outer catheter 52. The distal end of the inner catheter 54 is joined to the distal end of the positioning frame 22 by a fixing member 542, and the proximal end of the bearing frame 24 is joined to the distal end of the outer catheter 52. Through the relative positional relationship between the inner catheter 54 and the outer catheter 52, the axial length of the bearing frame 24 is controlled, thereby adjusting the diameter of the bearing frame 24 to make the diameter of the bearing frame 24 match the circular size of the target ablation region.

As shown in FIG. 3, the proximal end of each first main bar 221 is connected to two corresponding first branch bars 225, and the proximal ends of the two first branch bars 225 connected to the proximal end of each first main bar 221 extend away from each other. The proximal end of each first branch bar 225 is joined to the proximal end of a neighboring first branch bar 225, i.e., the first branch bars 225 connected to the proximal and distal ends of each first branch bar 225 are different from each other. The joint of the proximal ends of the first branch bars 225 is connected to the distal end of the bearing bar 241, and the joint of the distal ends of the first branch bars 225 is connected to the proximal end of the first main bar 221. The plurality of first branch bars 225 are arranged along the circumferential direction of the inner catheter 54, and the plurality of first branch bars 225 are connected end to end to form a wave-shaped annular structure. The proximal end of each first main bar 221 is connected to a corresponding peak of the wave-shaped annular structure, and the distal end of each bearing bar 241 is connected to a corresponding trough of the wave-shaped annular structure. In this embodiment, one end of the first branch bar 225 for connecting the bearing bar 241 extends towards the proximal end with respect to one end of the first branch bar 225 for connecting the first main bar 221. In a modified embodiment, one end of the first branch bar 225 for connecting the bearing bar 241 extend towards the distal end with respect to one end of the first branch bar 225 for connecting the first main bar 221. That is, the proximal end of each first main bar 221 is connected to a corresponding trough of the wave-shaped annular structure, and the distal end of each bearing bar 241 is connected to a corresponding peak of the wave-shaped annular structure.

Preferably, the intersection of each first main bar 221 and the multiple corresponding first branch bars 225 is bent to a side away from the inner catheter 54, the middle portion of each bearing bar 241 is bent to the side away from the inner catheter 54, and the intersection of the distal end of each bearing bar 241 and the multiple corresponding first branch bars 225 is bent towards a side close to the inner catheter 54. That is, the intersection of each first main bar 221 and the multiple corresponding first branch bars 225 protrudes away from the inner catheter 54, the middle portion of each bearing bar 241 protrudes away from the inner catheter 54, and the intersection of the distal end of each bearing bar 241 and the multiple corresponding first branch bars 225 is recessed toward the inner catheter 54, making the bearing frame 24 be more easily deformed than the positioning frame 22 during the deformation of the ablation assembly 20. When the relative positional relationship between the inner catheter 54 and the outer catheter 52 is adjusted to adjust the outer diameter of the bearing frame 24, since neighboring two first main bars 221 are restrained by two first branch bars 225 which are joined together, the first branch bar 225 pulls the first main bar 221 in the axial and radial directions, so that the first main bar 221 is not deformed too much in the radial and axial directions, which is beneficial for the positioning frame 22 to maintain a basket-like shape, thereby maintaining a better centering effect during changing the ablation diameter range of the ablation device 100. The problem of large deformation of the positioning frame 22 during adjusting the diameter of the bearing frame 24 and failure to abut against the inner walls of the pulmonary vein, which causes the ablation assembly to be unable to align around the orifice of the pulmonary vein and produce discontinuous ablation regions, is avoided to generate.

In this embodiment, one row of mesh holes 220 is formed in the axial direction of the positioning frame 22.

In other alternative embodiments, the proximal end of the first branch bar 225 is further connected to a circle of branch bar along the circumferential direction of the inner catheter 54, so as to form two rows of mesh holes 220 in the axial direction of the positioning frame 22. The proximal end of the first branch bar 225 is connected to the proximal end or distal end of the branch bar. In other alternative embodiments, the proximal end of one first main bar 221 is connected to more than two branch bars, and the first main bars 221, the first branch bars 225 and the branch bars may be straight, spiral or other curved. In this embodiment, the width of the first main bar 221 and/or the first branch bar 225 is less than or equal to the width of the bearing bar 241, thereby facilitating the insertion into a smaller diameter sheath for transporting in the body.

The bearing bars 241 of the bearing frame 24, the first branch bars 225, the branch bars and the first main bars 221 may be straight, spiral or other curved. The spiral may be obtained by heat setting after cutting. The spiral of the bearing bar 241 can also be formed by relative rotation of the inner catheter 54 and the outer catheter 52 through the operating handle 55 during the implantation process, thereby forming the spiral structure.

The branch bars 241 of the bearing frame 24 are connected to each other to form the mesh and mesh holes, and the shape of the mesh holes 240 may be arbitrary. The bearing bars 241 extend along the axial direction and/or radial direction, and at least some of the bearing bars 241 are provided with electrodes.

The bearing frame 24 may be made of metal materials such as nickel-titanium filaments. The cross section of the nickel-titanium filament is circular, semi-circular, or other geometric shape.

Preferably, as shown in FIG. 3, the supporting framework 21 further includes a connecting frame 26. The connecting frame 26 is connected between the bearing frame 24 and the outer catheter 52. During the deformation of the supporting framework 21, the deformation ratio of the connecting frame 26 is greater than the deformation ratio of the positioning frame 22.

Specifically, in the completely released state of the supporting framework 21, the connecting frame 26 is a frame structure with an inner cavity, and the deformation ratio of the positioning frame 22 is less than the deformation ratio of the connecting frame 26. In this embodiment, the cross section of the cutting pipe forming the connecting frame 26, the cross section of the cutting pipe forming the positioning frame 22 and the cross section of the cutting pipe forming the bearing frame 24 are the same. When the inner catheter 54 moves relative to the outer catheter 52, the deformation ratio of the cutting pipe of the positioning frame 22 is less than the deformation ratio of the connecting frame 26. The connecting frame 26 is also a mesh structure, and is provided with mesh holes 260. An opening size of the mesh holes 260 of the connecting frame 26 is less than the opening size of the mesh holes 240 of the bearing frame 24. That is, an opening area of the mesh holes 260 of the connecting frame 26 is less than the opening area of the mesh holes 240 of the bearing frame 24. The opening size of the mesh holes 260 of the connecting frame 26 is greater than the opening size of the mesh holes 220 of the positioning frame 22. That is, the opening area of the mesh holes 260 of the connecting frame 26 is less than the opening area of the mesh holes 240 of the bearing frame 24. In this embodiment, since the cross section of the cutting pipe of the positioning frame 22, the cross section of the cutting pipe of the bearing frame 24 and the cross section of the cutting pipe of the connecting frame 26 are the same, and the opening area of the mesh holes 220 is less than that of the mesh holes 260, the connecting frame 26 is more easily deformed than the positioning frame 22 when the outer catheter 52 and the inner catheter 54 are moved relative to each other. During the process of adjusting the supporting framework 21, since the meshes of the bearing frame 24 and connecting frame 26 are greater in size compared with the mesh of the positioning frame 22, the bearing frame 24 and connecting frame 26 are easy to change their radial sizes during deformation to close to the target tissue region.

The connecting frame 26 includes a plurality of second main bars 261 and a plurality of second branch bars 265. The plurality of second main bars 261 are arranged along the circumferential direction of the outer catheter 52. The proximal end of each second main bar 261 is connected to the outer catheter 52, and the distal end of each second main bar 261 is connected to multiple corresponding second branch bars 265. The proximal end of each bearing bar 241 is connected to multiple corresponding second branch bars 265, the other ends of the multiple second branch bars 265 connected to the same bearing bar 241 are connected to different second main bars 261, and the distal end of each bearing bar 241 is connected to the positioning frame 22.

In this embodiment, the positioning frame 22, the bearing frame 24 and the connecting frame 26 are integrally formed by cutting and shaping nickel-titanium tubes. The connecting frame 26 includes six second main bars 261 and two second branch bars 265 connected to the distal end of each second main bar 261. The plurality of second main bars 261 are arranged along the circumferential direction of the outer catheter 52. Preferably, these second main bars 261 are evenly arranged in the circumferential direction of the outer catheter 52. The proximal end of each second main bar 261 is connected to the distal end of the outer catheter 52, and the bearing bar 241 is connected to the second main bar 261 through the second branch bar 265. Specifically, the distal end of each second main bar 261 is connected with two second branch bars 265, the proximal end of each bearing bar 241 is connected with two second branch bars 265, and the distal ends of the two second branch bars 265 connected to the proximal end of each bearing bar 241 are connected to different second main bars 261, respectively. In this embodiment, in the completely released state of the supporting framework 21, the radial size of a frame enclosed by the plurality of second main bars 261 and second branch bars 265 is less than the radial size of a frame enclosed by the plurality of bearing bars 241. The distal end of the inner catheter 54 is joined to the distal end of the positioning frame 22, and the proximal end of the connecting frame 26 is joined to the distal end of the outer catheter 52. Through the relative positional relationship between the inner catheter 54 and outer catheter 52, the axial length of the bearing frame 24 is controlled, thereby adjusting the diameter of the bearing frame 24 to make the diameter of the bearing frame 24 match the circular size of the target ablation region.

As shown in FIG. 3, the distal end of each second main bar 261 is connected to two corresponding second branch bars 265, and the other ends of the two second branch bars 265 connected to the distal end of each second main bar 261 extend away from each other. The distal end of each second branch bar 265 is joined to the distal end of a neighboring second branch bar 265, i.e., the second branch bars 265 connected to the distal and proximal ends of each second branch bar 265 are different from each other. The joint of the distal ends of the second branch bars 265 is connected to the proximal end of one bearing bar 241, and the joint of the proximal ends of the second branch bars 265 is connected to the proximal end of one second main bar 261. The plurality of second branch bars 265 are arranged along the circumferential direction of the inner catheter 54, and the second branch bars 265 are connected end to end to form a wave-shaped annular structure. The distal end of each second main bar 261 is connected to a corresponding trough of the wave-shaped annular structure, and the proximal end of each bearing bar 241 is connected to a corresponding peak of the wave-shaped annular structure. In a modified embodiment, the distal end of each second main bar 261 is connected to a corresponding peak of the wave-shaped annular structure, and the proximal end of each bearing bar 241 is connected to a corresponding trough of the wave-shaped annular structure.

Optionally, the positioning frame 22 and/or the bearing frame 24 is provided with at least one ablation member 25. The ablation member 25 is an ablation electrode. The ablation energy source connected to the ablation member 25 may be radio frequency, pulse or microwave. In this embodiment, the bearing bar 241 includes a bearing section 243 provided adjacent to its distal end, and the ablation electrode is provided on the bearing section 243. Specifically, the ablation electrode is provided at a lateral side of the bearing section 243 away from the inner catheter 54.

When the ablation energy source connected to the ablation member 25 is radio frequency, the bearing bar 241 is provided with an insulating layer at a position without the ablation electrode. In this embodiment, the surface of the bearing bar 241 is vacuum-coated except for a positon with the ablation member 25, making the surface of the bearing bar 241 be covered with an insulating coating. The position of the surface of the bearing bar 241 with the ablation member 25 is exposed, and the bearing bar 241 conducts electrical signals for ablation. Preferably, the ablation member 25 is provided at a position of the bearing bar 241 where its diameter is the largest after the radial size thereof is compressed.

When the ablation energy source connected to the ablation member 25 is pulse, the bearing frame 24 is provided with the ablation member 25. That is, the bearing bar 241 is provided with an electrode separately, and the electrode is made of platiniridium, gold or other platinum alloy. An inner side of each electrode is welded with a conducting wire which has an insulating layer. The bearing bar 241 includes a nickel-titanium filament and an insulating sleeve or other polymer insulating materials surrounding the nickel-titanium filament. The electrode is mounted around the insulating sleeve to ensure the insulation between the electrode and the bearing bar 241. The conducting wire with insulating layer is disposed between the bearing bar 241 and the insulating sleeve or other polymer insulating materials. The surface of the nickel-titanium filament is vacuum-coated to be covered with a layer of insulation coating. That is, the inner side of each electrode is connected to an ablation electrode connector 551 of the handle 55 through the conducting wire which passes through the inner catheter 54 along the nickel-titanium filament from the surface of the insulating sleeve, and in turn electrically connected to an external pulse signal source through the ablation electrode connector 551. The electrode and the conducting wire are connected by welding or other special processes. When the inner catheter 54 is used to pull the bearing frame 24 for diameter adjustment, the diameter range at the cross section of the bearing bar 241 is 10 mm-36 mm.

In one embodiment, the voltage range of the pulse signal received by the ablation electrode is 900V~2400V, including all values and sub-ranges; and the pulse frequency is 1 kHz~500 kHz, including all values and sub-ranges. The pulse energy may be either unipolar high voltage pulse power supply or bipolar high voltage pulse power supply. For the waveform of the bipolar high voltage pulse signal, positive and negative pulses are alternated in each period, and always meet that: the voltage of the positive pulse/the voltage of the negative pulse=the width of the negative pulse/the width of the positive pulse=$\beta$, wherein $\beta$ may be adjusted continuously from 1 to 8. Correspondingly, the maximum voltage to which the conducting wire is subjected is 3000V, and all of the ablation electrodes can be divided into one or more positive-negative sets.

The energy pulse trains received by the ablation electrode include single-phase pulses or biphasic pulses, and each of the ablation electrodes can be configured with single-phase pulses or biphasic pulses with different parameters such as voltage, pulse width, repetition frequency, duty cycle and number of pulses.

Pulse ablation uses high intensity pulsed electric field to cause irreversible electrical breakdown of the cell membrane, which is called irreversible electroporation in the medical field, so as to make the cell apoptosis and thus achieve the non-thermal effect of ablation cells, which is not affected by heat sink effect. The high voltage pulse trains produce less heat, and do not need to be washed with physiological saline for cooling, which can effectively reduce the occurrence of gas explosion, eschar and thrombus. Pulse ablation treatment time is short, the treatment time of applying a group of pulse sequences is less than 1 minute, and the whole ablation time is generally less than 5 minutes. Moreover, due to the difference in the response threshold of different tissues to the pulsed electric field, it is possible to ablation the myocardium without interfering with other adjacent tissues, so that the tissues adjacent to the pulmonary vein can be avoided from being injured by mistake. In addition, compare with other energies, pulse ablation does not require heat conduction to ablation deep tissues, and electroporation occurs in all cardiac muscle cells distributed over a certain electric field intensity, which reduces the requirement for catheter attachment pressure during ablation. Thus, even if the ablation device does not fully fit the tissue wall after entering the atrium, the ablation effect will not be affected. The electrode for applying pulse energy can also collect endocardial electrical signals. Before ablation, the endocardial electrical signals are collected and transmitted to the ECG synchronizer, so that the pulse output is synchronized at the absolute refractory period of myocardial contraction, thereby not interring the heart rate and reducing sudden arrhythmia. After ablation, it is also possible to determine whether the tissue has been completely electrically isolated according to the endocardial electrical signals.

Optionally, the inner catheter 54 is hollow and tubular. The mapping device 30 includes a mapping catheter 31, a mapping electrode 33 provided at the distal end of the mapping catheter 31, and a mapping electrode connector 35 connected to the proximal end of the mapping catheter 31. The mapping catheter 31 is inserted into the inner catheter 54, and the mapping electrode 33 extends out from the distal end of the inner catheter 54 for attaching to the tissue wall to detect the electrophysiological signals in the target tissue region. Specifically, the mapping electrode 33 extends spirally for at least one circle after extending out from the distal end of the inner catheter 54. A plurality of mapping electrodes 33 are provided at the distal end of the mapping catheter 31 and spaced from each other. The mapping catheter 31 is configured to be inserted into the inner catheter 54, and the mapping electrode 33 extends out from the distal opening of the inner catheter 54 for attaching to the tissue wall to detect electrophysiological signals in the target tissue region.

In other embodiments, the ablation electrodes on the supporting framework 21 may be used for both ablation and mapping of electrophysiological signals. If the ablation electrodes on the bearing frame 24 may be used for mapping, the inner catheter 24 may accordingly be replaced by a pulling wire. In one embodiment, the ablation electrode is used to perform other functions such as cardiac pacing.

Optionally, the proximal end of the bearing frame 24 is provided with a connecting frame 26, which is used for maintaining the relative positional relationship between neighboring bearing bars 241. After pulling the inner catheter 54, the distance between the multiple ablation members 25 is not too close to avoid generating electric arc. In addition, the uniformity of distribution of the plurality of bearing bars 241 in the circumferential direction is improved, the bearing frame 24 in whole is not easy to twist and deform, the ablation accuracy of the ablation device 100 is improved, and the ablation efficiency is high.

Optionally, in other embodiments, the first main bar 221 and/or first branch bar 225 of the positioning frame 22 are provided with electrodes, and the arrangement of the electrodes is referred to the arrangement of the electrodes on the bearing frame 24, which will not be repeated here. The electrode is an ablation electrode or a mapping electrode. If the electrode is a mapping electrode, the mapping catheter 31 in FIG. 1 is omitted, and the inner catheter 54 may be replaced by a pulling wife, which is beneficial to reduce the diameter of the outer catheter 52.

As shown in FIG. 1, FIG. 4 and FIG. 5, the outer diameter of the bearing frame 24 can be adjusted by pulling the inner catheter 54 at the proximal end of the handle 55 to adapt to the pulmonary veins of different diameters. During working, the diameter of the bearing frame 24 can be adjusted to increase, so as to facilitate the ablation member 25 to generate an electric field at the orifice of the pulmonary vein by transferring pulse energy to ablate tissues; or, the diameter of the bearing frame 24 can be adjusted to decrease, so that the ablation member 25 can be placed in the pulmonary vein for tissue ablation.

The ablation device 100 of the present application may also be delivered to a specific position of the heart by percutaneous puncture, so as to ablation the left atrial appendage out of the pulmonary vein, or the foci combined with typical atrial flutter and non pulmonary vein origin (such as superior vena cava and coronary sinus ostium), achieving the effect of electrical isolation.

The inner catheter 54 is a hollow structure. Optionally, a mapping catheter 31 or a guiding wire may be inserted into the inner cavity of the inner catheter 54 for mapping or position.

Figure 6:
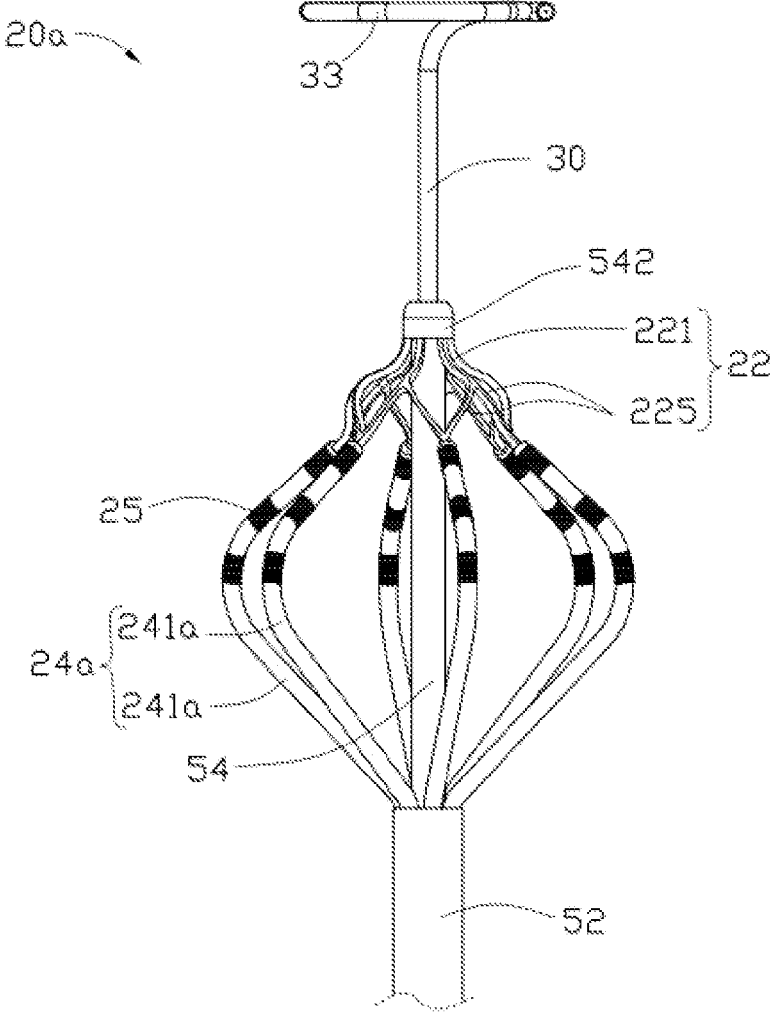
FIG. 6 a schematic view of an ablation assembly according to a second embodiment of the present application.
Figure 7:
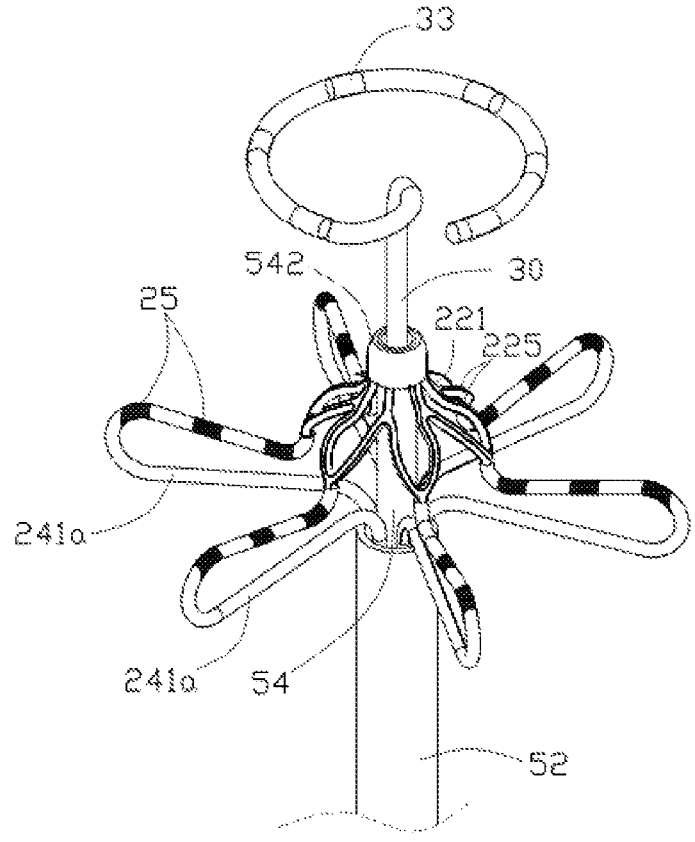
FIG. 7 is a schematic view of the ablation assembly of FIG. 6 in one of its use states.
Figure 8:
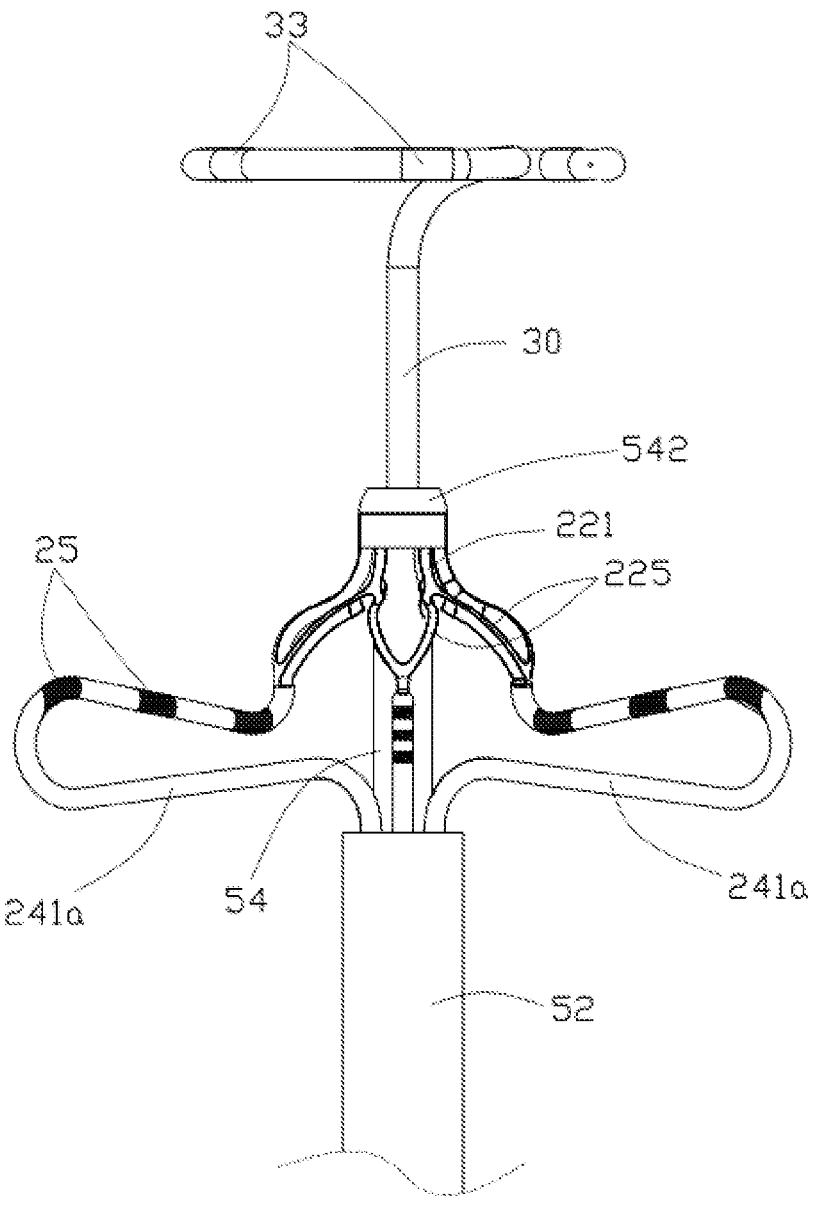
FIG. 8 is a side view of the ablation assembly of FIG. 7.

Please referring to FIGS. 6-8, an ablation device 100a according to a second embodiment of the present application has a structure similar to that of the first embodiment, and the difference therebetween is that the ablation assembly 20a of the second embodiment omits the connecting frame compared with the first embodiment, so that the proximal end of the bearing frame 24a is directly connected to the distal end of the outer catheter 52. In other words, the proximal end of each bearing bar 241 is connected to the distal end of the outer catheter 52. Specifically, the bearing frame 24a includes a plurality of bearing bars 241a sequentially arranged in the circumferential direction. The distal ends of the bearing bars 241a are spaced from each other and connected to the distal ends of different first branch bars 225 of the positioning frame 22. The proximal ends of the plurality of bearing bars 241a are joined together and connected to the distal end of the outer catheter 52.

When the relative positional relationship between the inner catheter 54 and the outer catheter 52 is adjusted to adjust the outer diameter of the bearing frame 24a, since adjacent branch bars of the positioning frame 22 are joined together to constrain each other, the bearing bars of the bearing frame 24a are more likely to deform compared with the positioning frame 22, so that the bearing frame 24a is easy to produce obvious changes in radial and axial sizes when the ablation assembly 20a changes its ablation diameter range. Because the first main bar 221 and first branch bar 225 are restrained to each other, the positioning frame 22 is more likely to maintain a mesh shape, and the deformation ratio is smaller, thereby maintaining a better centering effect. The problem of large deformation of the positioning frame 22 during adjusting the diameter of the bearing frame 24a and failure to abut against the inner walls of the pulmonary vein, which causes the adjustment assembly 50 to be unable to align around the orifice of the pulmonary vein and produce discontinuous ablation regions, is avoided to generate.

The plurality of bearing bars 241a of the bearing frame 24a are arranged in sequence in the circumferential direction of the inner catheter 54. In this embodiment, the plurality of bearing bars 241a are evenly arranged in the circumferential direction of the inner catheter 54, and the bearing frame 24 includes 3-8 bearing bars. In this embodiment, the bearing frame 24 includes 6 bearing bars.

Figure 9:
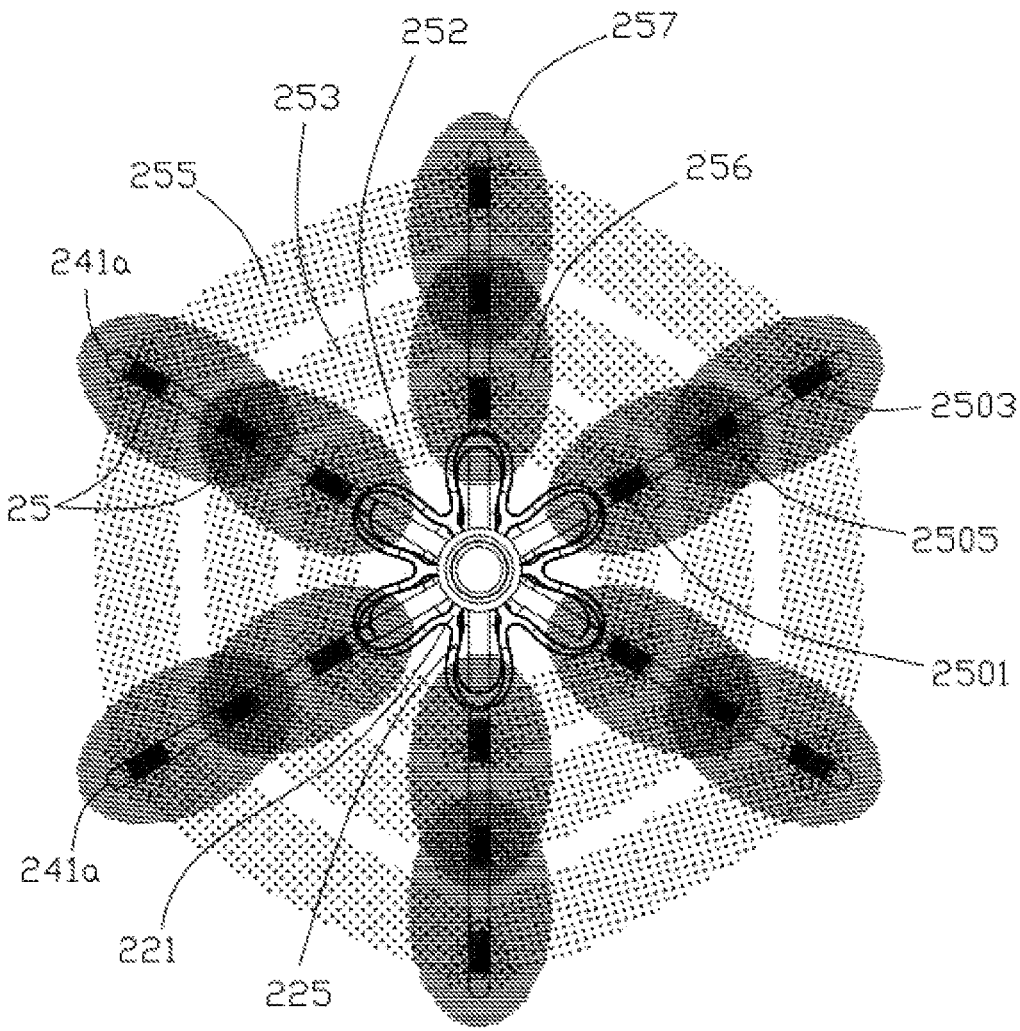
FIG. 9 is a schematic view of a stereo-electric field of the ablation assembly of FIG. 7.
Figure 10:
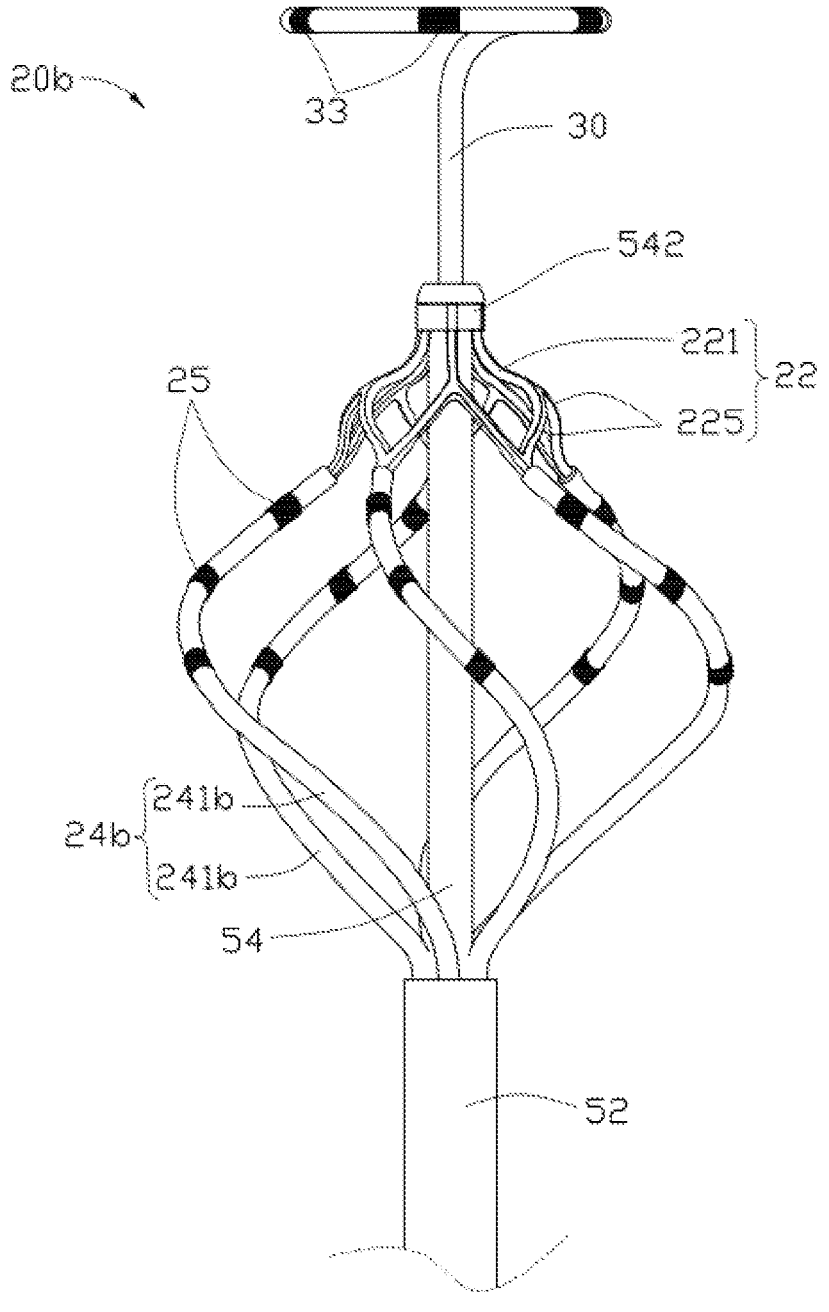
FIG. 10 is a schematic view of an ablation assembly according to a third embodiment of the present application.
Figure 11:
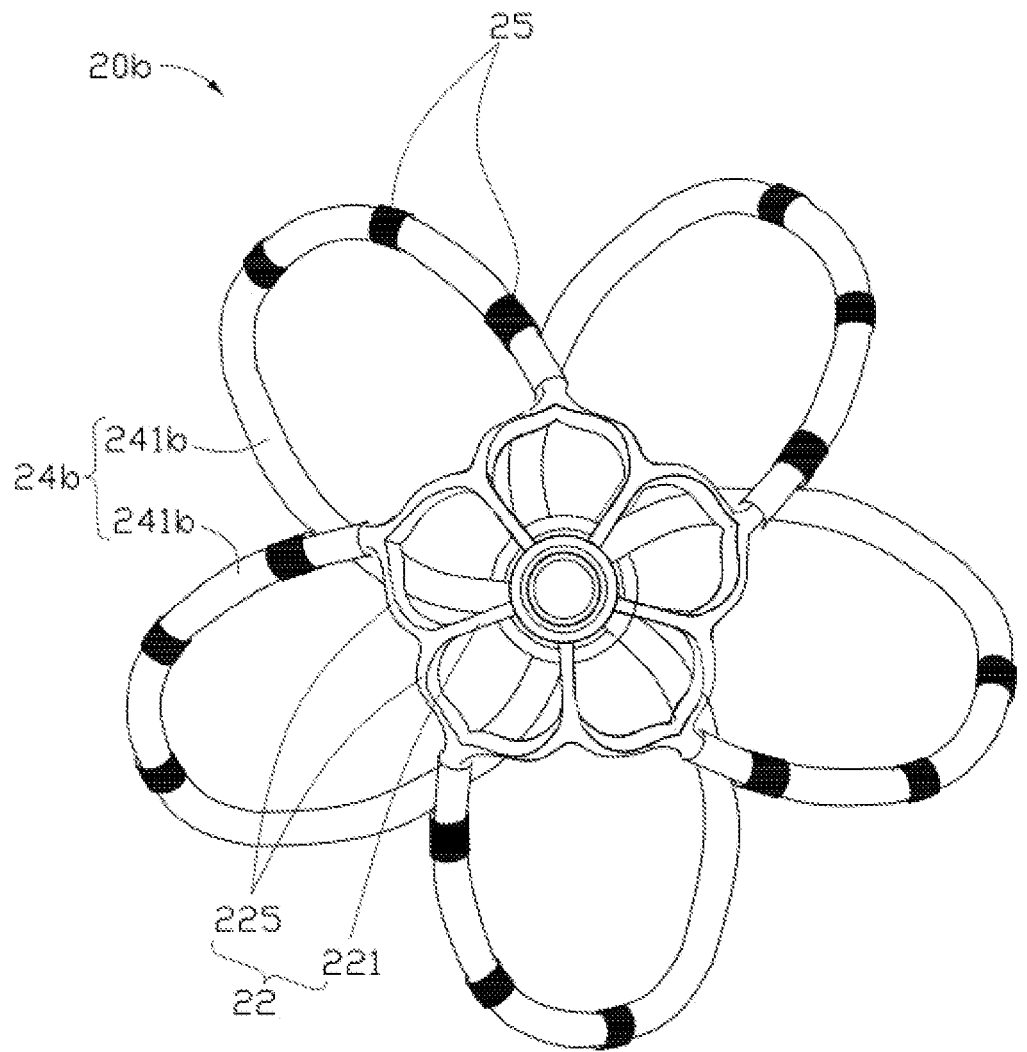
FIG. 11 is a top view of the ablation assembly of FIG. 10.
Figure 12:
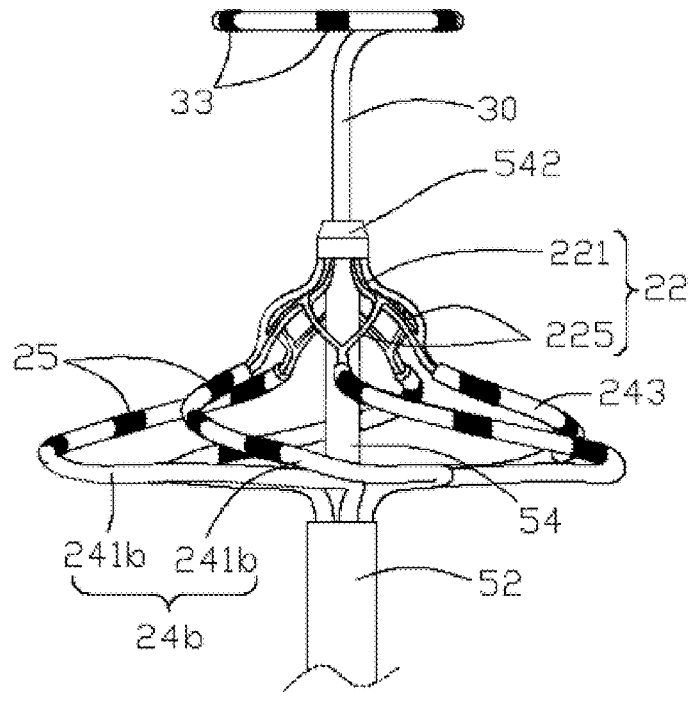
FIG. 12 is a schematic view of the ablation assembly of FIG. 10 in one of its use states.

As shown in FIG. 9, each bearing bar 241a is provided with a plurality of ablation members 25 along its axial direction. In this embodiment, the ablation members 25 are ablation electrodes. The polarities of two adjacent ablation electrodes on the same bearing bar 241a are opposite, and the polarities of adjacent ablation electrodes on two adjacent bearing bars 241a are opposite. The multiple ablation electrodes on the bearing frame 24a enclose several circles in the longitudinal axis of the inner catheter 54, and the multiple electrodes on each circle form an annular-shaped electric field. In this embodiment, each bearing bar 241a is provided with three ablation members 25 along its axial direction, and three circles of electrodes are provided on the bearing frame 241a. In the completely released state, the three circles of electrodes include a first circle of electrode 2501 near the inner catheter 54, a third circle of electrode 2503 away from the inner catheter 54, and a second circle of electrode 2505 between the first circle of electrode 2501 and the third circle of electrode 2503. Since adjacent electrodes in the first circle of electrodes are coupled to each other to form an electric field, these electric fields are superposed to form a closed-loop of first annular electric field 252 around the axial direction; adjacent electrodes in the second circle of electrodes are coupled to each other to form an electric field, and these electric fields are superposed to form a closed-loop of second annular electric field 253 around the axial direction; and adjacent electrodes in the third circle of electrodes are coupled to each other to form an electric field, and these electric fields are superposed to form a closed-loop of third annular electric field 255 around the axial direction.

At the same time, since the polarities of the adjacent ablation electrodes on each bearing bar 241a are opposite, the adjacent ablation electrodes on each bearing bar 241a are coupled with each other to form electric fields in the radial direction when a pulsed electric field is formed, which are first radial electric field 256 and second radial electric field 257, respectively. The electric fields generated by all of the ablation electrodes of the entire bearing frame 24a are distributed in a network in the circumferential direction and the radial direction. By means of adjusting the diameter to control the specific shape of the bearing bar 241a, the ablation electrodes on the bearing bars 241a are capable of forming a 3D electric field in space, or called stereo-electric field, which makes the ablation range be larger. Even if the axis of the inner catheter 54 does not coincide with the central axis of the pulmonary vein, continuous annular electrical isolation can also be carried out within a certain deviation range.

Please referring to FIGS. 10-13, an ablation device according to a third embodiment of the present application has a structure similar to that of the second embodiment, and the difference therebetween is that the bearing bar 241b in the third embodiment is a spiral bar. The proximal and distal ends of the spiral bar deflect a predetermined angle in the circumferential direction, and preferably, the predetermined angle is 30-70 degrees.

The twist angles (i.e., spiral angles) of each bearing bar 241b at different positions from the proximal end may be different. Specifically, the spiral angle of the bearing bar 241b at a position between the proximal and distal ends is greater than the spiral angle at the proximal end or distal end of the bearing bar 241b. That is, the spiral bearing bar 241b has the largest spiral angle at the position between the proximal and distal ends. In one embodiment, the spiral angle of bearing bar 241b at a midpoint of the proximal and distal ends is greater than the spiral angle at the proximal end or distal end of bearing bar 241b, and the spiral angle decreases from the midpoint to both sides. In one of the preferred embodiments, the spiral angles of the bearing bar 241b are symmetrically distributed at two sides of the midpoint. Such spiral distribution structure makes the ablation assembly 20b have better compliance and attach to the ablation tissue area closely.

Figure 13:
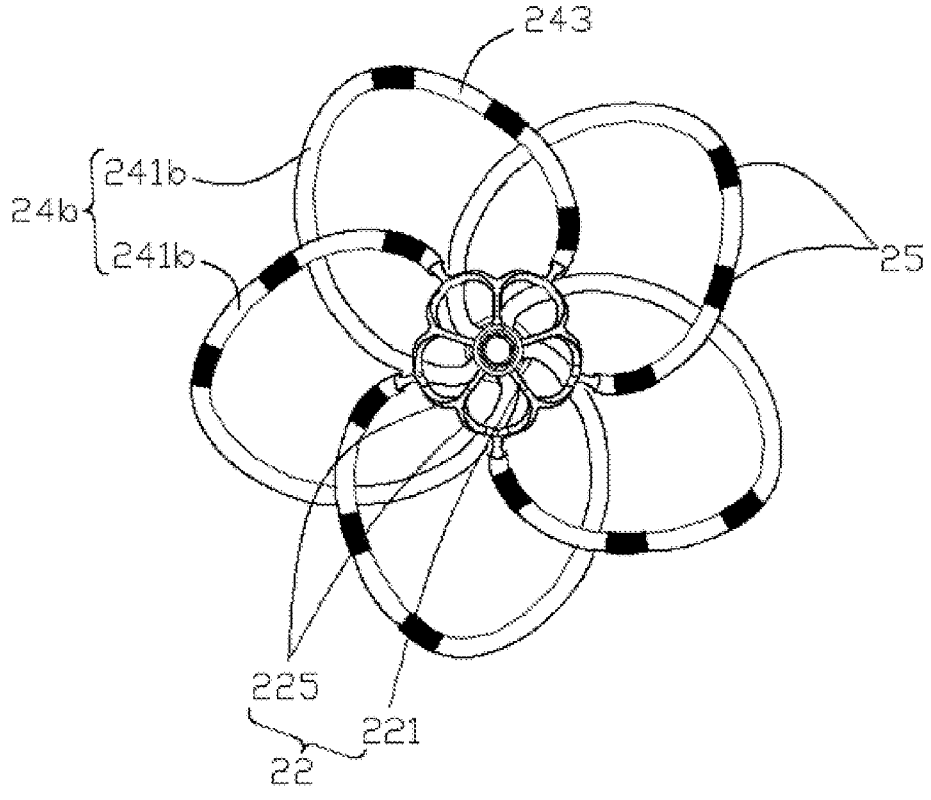
FIG. 13 is a top view of the ablation assembly of FIG. 12.

In this embodiment, the spiral bearing bars 241b are evenly distributed along the circumferential direction of the inner catheter 54. The bearing bars 241b are 3-10 in number, and the overall shape of the bearing bars 241b on the cross-sectional plane passing through the axis is elliptical, circular or any other symmetrical geometric shapes. In this embodiment, the bearing frame 24b Includes six bearing bars 241b, each bearing bar 241b Is provided with three ablation members 25 which are spaced from each other along the axial direction, and each ablation member 25 is an ablation electrode. As shown in FIG. 13, the bearing bar 241b Includes a bearing section 243 provided adjacent to the distal end thereof, and the ablation member 25 is disposed on the bearing section 243. Specifically, the ablation member 25 is mounted around a peripheral wall of the bearing section 243. In this embodiment, the ablation member 25 is an ablation electrode, which has a shape conforming to the spiral shape of each bearing bar 241b and is disposed on the bearing section 243 adjacent to the distal end of the bearing bar 241b, ensuring that during ablation the orifice of pulmonary vein, the distance between the plurality of ablation electrodes of adjacent bearing bars 241b is not too close to avoid generating electric arc after the inner catheter 54 is pulled, and also ensuring that the ablation electrode of the ablation assembly 20b can be well attached to and compliant with the atrial tissue.

In one of the embodiments, the ablation electrodes on each bearing bar 241b have the same polarity and are connected to the same conducting wire, and are different from the electrodes on an adjacent spiral bearing bar 241b In polarity.

In a delivery state, the ablation assembly 20 is disposed in the delivery catheter, being stretched in the axial direction and compressed in the radial direction. In some embodiments, in the delivery state, at least one of the bearing bars 241b extends spirally in the delivery catheter. Further, some or all of the bearing bars 241b extend spirally in the delivery catheter.

Figure 14:
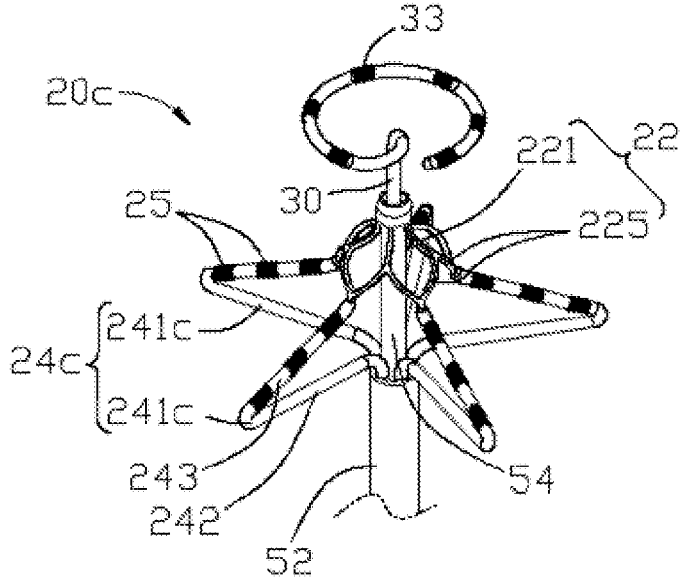
FIG. 14 is a schematic view of an ablation assembly according to a fourth embodiment of the present application.
Figure 15:
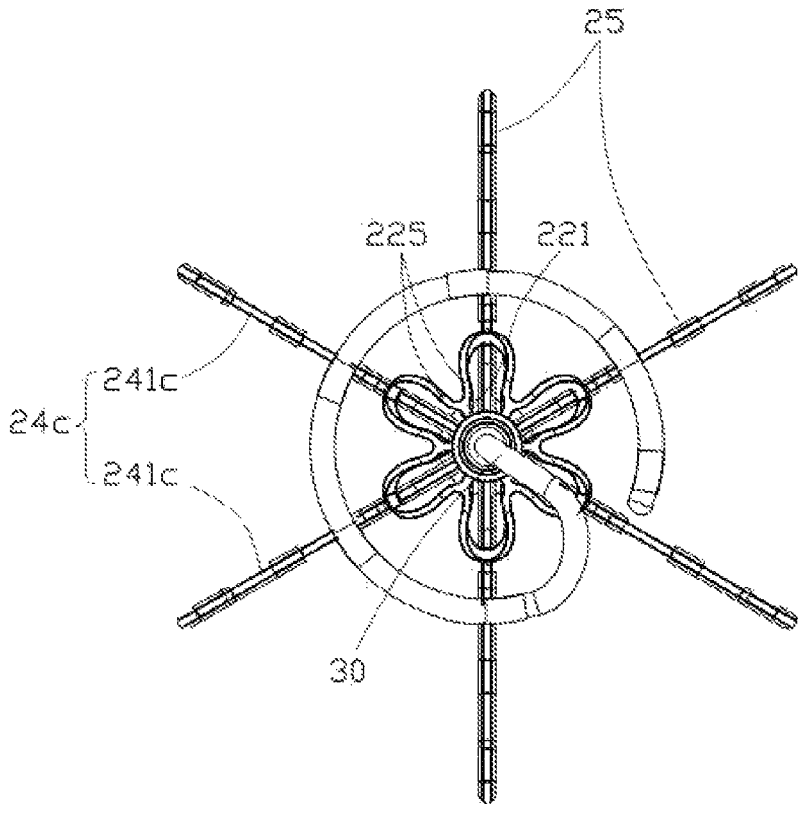
FIG. 15 is a top view of the ablation assembly of FIG. 14.

Please referring to FIGS. 14 and 15, an ablation device according to the fourth embodiment of the present application has a structure similar to that of the second embodiment, and the difference therebetween is that the bearing bar 241c in the fourth embodiment is a bending bar. The bending bar includes an extending section 242 extending radially and outwardly from the outer catheter 52 and a bearing section 243 connected between an end of the extending section 242 away from the outer catheter 52 and the positioning frame 22. An angle between the extending section 242 and the bearing section 243 is greater than 0 degrees and less than 90 degrees. Preferably, the angle between the extending section 242 and the bearing section 243 is greater than 30 degrees and less than 60 degrees.

The bearing bars 241c are distributed along the circumferential direction of the outer catheter 52. The bearing bars 241c are 3-10 in number, and these bearing bars 241c enclose a bearing frame 24c with a conical longitudinal section. In this embodiment, the bearing frame 24c includes six bearing bars 241c, and each bearing section 243 of the bearing bar 241c is provided with three ablation members 25 which are spaced from each other along the axial direction. Each ablation member 25 is an ablation electrode, and the shape of the ablation electrode conforms to the outer profile of each bearing bar 241c. The ablation electrodes are disposed at the middle and opposite ends of the bearing section 243.

During ablation of the orifice of the pulmonary vein, the inner catheter 54 is pulled to make the bearing frame 24c deform, so as to reduce the axial size of the bearing frame 24c and reduce the angle between the extending section 242 and the bearing section 243 of each bearing bar 241c, until the ablation electrode of the ablation assembly 20c can be well attached to and compliant with the atrial tissue.

Figure 16:
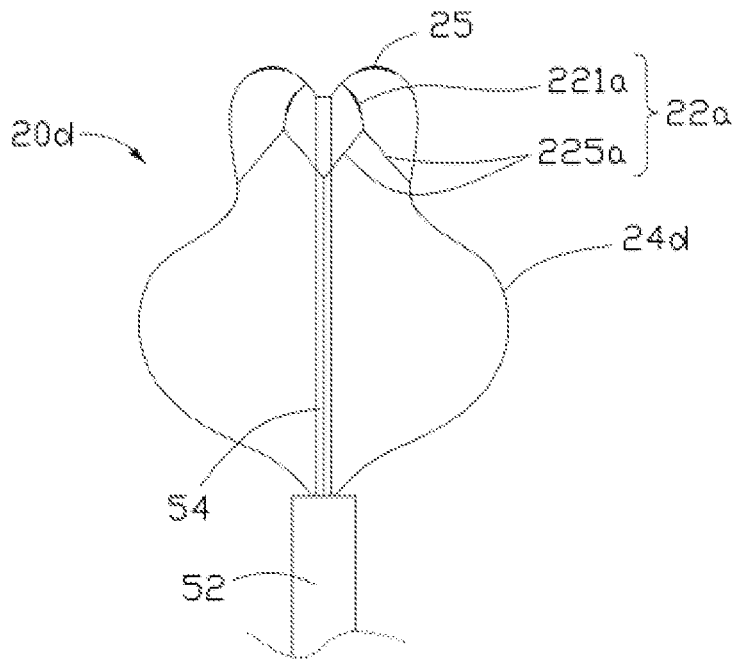
FIG. 16 is a schematic view of the ablation assembly according to a fifth embodiment of the present application.
Figure 17:
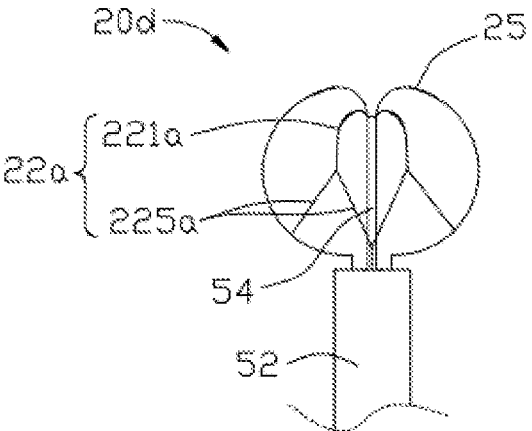
FIG. 17 is a schematic view of an ablation assembly of FIG. 16 in one of its use states.

Please referring to FIGS. 16 and 17, an ablation device according to a fifth embodiment of the present application has a structure similar to that of the first embodiment, except that the positioning frame 22a of the fifth embodiment is an inverted wrap structure. That is, the distal end of the positioning frame 22a connects the inner catheter 54 along a direction from the distal end to the proximal end. In this embodiment, the positioning frame 22a includes a plurality of first main bars 221a and a plurality of first branch bars 225a. Specifically, the distal end of each first main bar 221a extends beyond or is flush with the distal end of the inner catheter 54, and an end portion of the first main bar 221a extends from the distal end towards the proximal end thereof to connect to the inner catheter 54. The positioning frame 22a is provided with an ablation member 25, i.e., the ablation member 25 is disposed at the distal end of the positioning frame 22a. Specifically, the ablation member 25 is disposed at a side of the first main bar 221a away from the inner catheter 54, and preferably at the distal end of the positioning frame 22a. In some embodiments, there is no ablation member 25 on the positioning frame 22a.

In this embodiment, the distal end of the first main bar 221a is sandwiched into a double-layer steel sleeve provided at the distal end of the inner catheter 54. The first main bar 221a is bent into an arc shape at the distal end of the positioning frame 22a, and such structure can avoid instrument damage to atrial tissue due to the protruded tip at the distal end of the positioning frame 22a, and better conform to the anatomical structure of the heart ablation region. The inverted wrap structure also can be used for ablation treatment in patients with myocardial hypertrophy.

As shown in FIG. 17, after the bearing frame 24d withdraws into the outer catheter 52, the positioning frame 22a is shaped like a ball when the positioning frame 22a is exposed from the distal end of the outer catheter 52. These ablation members 25 are used for point ablation (focal ablation) of the interior of the heart. That is, in this embodiment, the ablation assembly 20d can be used not only for circular ablation but also for focal ablation. Therefore, a new indication of the ablation assembly 20a is increased, which has a better application prospect.

In other modified embodiments, the ablation member 25 may also be set at a position where the positioning frame 22a has the largest radial size, so as to facilitate access to the target tissue region.

Figure 18:
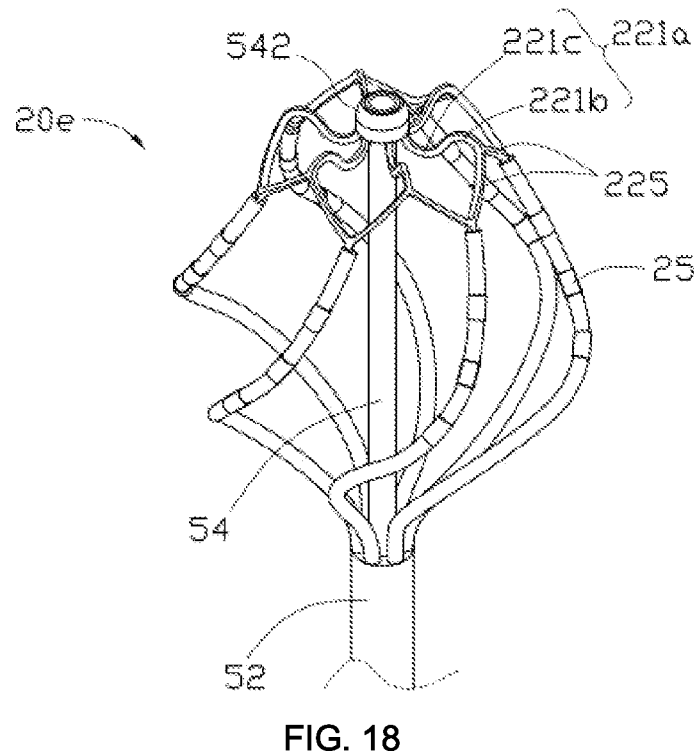
FIG. 18 is a schematic view of an ablation assembly according to a sixth embodiment of the present application.
Figure 19:
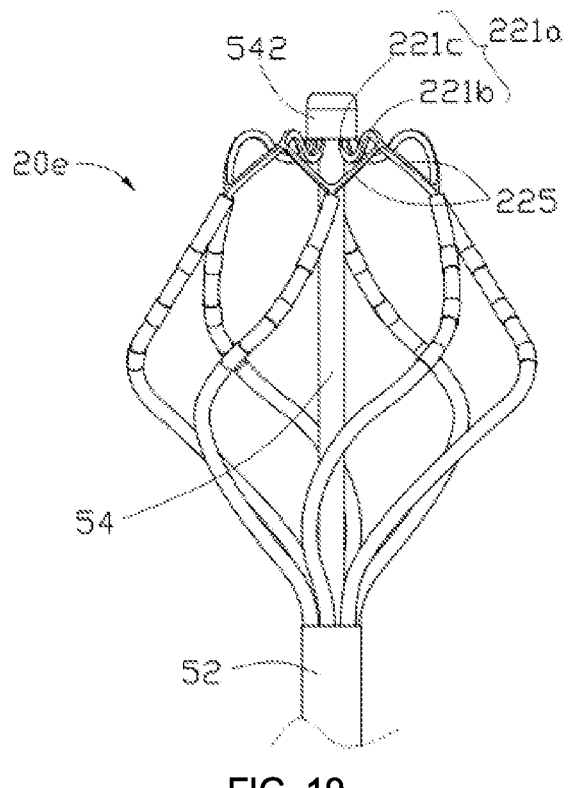
FIG. 19 is a side view of the ablation assembly of FIG. 18.

Please referring to FIGS. 18-19, an ablation device according to the sixth embodiment of the present application has a structure similar to that of the fifth embodiment. The ablation assembly 20e is at least in the case of axial compression within a certain size, the distal end of each first main bar 221a extends beyond or is flush with the distal end of the inner catheter 54. That is, the distal end of each first main bar 221a does not exceed the distal end of the inner catheter 54. The difference is that in the sixth embodiment, the first main bar 221a is curved. Specifically, the first main bar 221a includes an upper convex section 221b and a lower convex section 221c whose ends are connected with each other. One end of the upper convex section 221b is connected to the end portion of the first branch bar 225, and one end of the lower convex section 221c is connected to the fixing member 542. In the circumferential direction, the upper convex section 221b is connected to the outer side of the lower convex section 221c, the upper convex section 221b protrudes towards the distal direction, and the lower convex section 221c protrudes towards the proximal direction. The multiple lower convex sections 221c define a receiving space at a position adjacent to the fixing member 542, and the receiving space occupies a certain range in the axial direction and the circumferential direction. The fixing member 542 is used to be received in the receiving space at least when the ablation assembly 20 is axially compressed to some extent, thus the distal end of each first main bar 221a does not exceed the distal end of the inner catheter 54 when the ablation assembly 20 is at least in the case of axial compression within a certain size, for example, in the completely released state, or in the case of axial compression to the minimum size.

The upper convex section 221b extends distally from the first branch bar 225 and then extends proximally to form a protrusion protruding towards the distal end and connect the lower convex section 221c. The lower convex section 221c extends proximally from the upper convex section 221b and then extends distally to form a protrusion protruding towards the proximal end and connect the fixing member 542. The lower convex section 221c extends from the proximal end to the distal end to connect the fixing piece 542, which is beneficial to reduce the bending angle of the lower convex section 221c during adjustment the diameter of the ablation assembly 20, improving the fatigue strength of the lower convex section 221c and forming the receiving space, avoiding the damage of the fixing member 542, and improving the safety and reliability of the system. Since the positioning frame is not easy to deform in the deformation process, the positions of the upper convex section 221b and lower convex section 221c are not easy to offset, and the fixing member 542 received in the receiving space is not easy to exceed the distal end of the first main bar 221a from the distal end thereof.

In this embodiment, the positioning frame is not provided with the ablation member 25. Specifically, the ablation member 25 is a cylindrical, annular electrode. It can be understood that the ablation member 25 may be other types of electrodes, or may be bare bearing bar without insulation treatment. In modified embodiments, the ablation member 25 may be provided on the positioning frame.

It should be noted that the specific technical solutions in the embodiments can be applied to each other without departing from the invention principle of the present application.

The above is embodiments of the present application, and it should be pointed out that certain modifications and embellishments can be made without departing from the principles of the embodiments of the present application for persons of ordinary skill in the art. These modifications and embellishments are also considered to be within the scope of the present application.

What is claimed is:

1. An ablation device, comprising an ablation assembly and an adjustment assembly provided at the proximal end of the ablation assembly;

the adjustment assembly comprising an outer catheter and an inner catheter which both extend in an axial direction;

the ablation assembly comprising a supporting framework and a plurality of ablation members provided on the supporting framework, the supporting framework comprising a positioning frame and a bearing frame, the positioning frame being provided at the distal end relative to the bearing frame; and the distal end of the outer catheter being connected to the proximal end of the bearing frame, the distal end of the inner catheter being connected to the distal end of the positioning frame, during moving of the inner catheter relative to the outer catheter, the supporting framework deforming, and the deformation ratio of the positioning frame being less than the deformation ratio of the bearing frame;

wherein the bearing frame comprises a plurality of bearing bars arranged along a circumferential direction, each bearing bar comprises an extending section extending radially and outwardly from the outer catheter and a bearing section bending radially and inwardly from the extending section to the positioning frame, the plurality of ablation members all are provided on the bearing sections of the plurality of bearing bars, and an electric field is generated between the ablation members which are different in polarity to ablate tissue during use of the ablation device.

2. The ablation device according to claim 1, wherein the rigidity of a cutting pipe or material filament of the positioning frame is greater than or equal to the rigidity of a cutting pipe or material filament of the bearing frame.

3. The ablation device according to claim 1, wherein during the deformation of the supporting framework, the deformation ratio of the positioning frame in the axial direction or the radial direction is less than the deformation ratio of the bearing frame in the axial direction.

4. The ablation device according to claim 1, wherein the outer catheter is hollow and tubular, the inner catheter is disposed in the outer catheter, and the axial and radial sizes of the supporting framework are changed during axial movement of the inner catheter relative to the outer catheter.

5. The ablation device according to claim 4, wherein during the axial movement of the inner catheter towards the proximal end relative to the outer catheter, the axial size of the bearing frame decreases and the radial size of the bearing frame increases; and during the axial movement of the inner catheter towards the distal end relative to the outer catheter, the axial size of the bearing frame increases and the radial size of the bearing frame decreases.

6. The ablation device according to claim 1, wherein the supporting framework is at least one of a mesh structure, a rod structure and a frame structure which is formed by weaving elastic metal filaments or cutting an elastic metal pipe.

7. The ablation device according to claim 6, wherein the positioning frame and bearing frame both are provided with mesh holes, and an opening area of the mesh holes of the positioning frame is less than an opening area of the mesh holes of the bearing frame.

8. The ablation device according to claim 7, wherein the diameter of the material filament of the positioning frame is greater than or equal to the diameter of the material filament of the bearing frame.

9. The ablation device according to claim 1, wherein the positioning frame comprises a plurality of first main bars and a plurality of first branch bars, the plurality of first main bars are arranged along the circumferential direction, the distal end of each first main bar is connected to the inner catheter, and the proximal end of each first main bar is connected to multiple corresponding first branch bars; and wherein the distal end of each bearing section is connected to multiple corresponding first branch bars, and the other ends of the multiple first branch bars connected to the same bearing section are connected to different first main bars.

10. The ablation device according to claim 9, wherein
the proximal end of the extending section of each bearing bar is connected to the outer catheter; or
the proximal end of each first main bar is connected to two corresponding first branch bars, the other ends of the two first branch bars connected to the proximal end of each first main bar extend away from each other, and the proximal end of each first branch bar is joined to the proximal end of a neighboring first branch bar; or
the intersection of each first main bar and the multiple corresponding first branch bars is bent to a side away from the inner catheter, the middle portion of each bearing bar is bent to the side away from the inner catheter, and the intersection of the distal end of each bearing section and the multiple corresponding first branch bars is bent towards a side close to the inner catheter.

11. The ablation device according to claim 1, wherein the supporting framework further comprises a connecting frame, the connecting frame is connected between the bearing frame and the outer catheter, and the deformation ratio of the connecting frame is greater than the deformation ratio of the positioning frame during the deformation of the supporting framework.

12. The ablation device according to claim 11, wherein
the connecting frame is provided with mesh holes, and the opening area of the mesh holes of the positioning frame is less than an opening area of the mesh holes of the connecting frame; or
the connecting frame comprises a plurality of second main bars and a plurality of second branch bars, the plurality of second main bars are arranged along the circumferential direction, the proximal end of each second main bar is connected to the outer catheter, and the distal end of each second main bar is connected to multiple corresponding second branch bars; and wherein the proximal end of the extending section of each bearing bar is connected to multiple corresponding second branch bars, the other ends of the multiple second branch bars connected to the same bearing bar are connected to different second main bars, and the distal end of the bearing section of each bearing bar is connected to the positioning frame.

13. The ablation device according to claim 1, wherein each bearing bar is a spiral bar, and the proximal and distal ends of the bearing bar deflect a predetermined angle in the circumferential direction.

14. The ablation device according to claim 13, wherein the spiral angle of the bearing bar at a position between the proximal and distal ends thereof is greater than the spiral angle at the proximal end or distal end thereof.

15. The ablation device according to claim 9, wherein an end portion of the first main bar extends from the distal end towards the proximal end thereof to connect the inner catheter.

16. The ablation device according to claim 1, wherein the ablation member is configured as ablation electrode to ablate tissue by using pulsed energy source.

17. The ablation device according to claim 1, wherein polarities of two adjacent ablation members on the same bearing section are opposite from each other, and polarities of adjacent ablation members on two adjacent bearing sections are opposite from each other, the plurality of ablation members on the bearing frame form several circles in the circumferential direction, and the multiple ablation members of each circle form an annular-shaped electric field.

18. An ablation system, comprising a mapping device and the ablation device according to claim 1, the inner catheter being hollow and tubular, the mapping device comprising a mapping catheter and a mapping electrode provided at the distal end of the mapping catheter, the mapping catheter being inserted into the inner catheter, and the mapping electrode extending out from the distal end of the inner catheter to contact a tissue wall to detect electrophysiological signals in the target tissue region.

19. An ablation device, comprising an ablation assembly and an adjustment assembly provided at a proximal end of the ablation assembly;
the adjustment assembly comprising an outer catheter and an inner catheter both extending axially;
the ablation assembly comprising a supporting framework and an ablation member provided on the supporting framework, the supporting framework comprising a positioning frame and a bearing frame, the positioning frame being provided at a distal of the bearing frame; and
a distal end of the outer catheter being connected to a proximal end of the bearing frame, a distal end of the inner catheter being connected to a distal end of the positioning frame, wherein the supporting framework deforms during moving of the inner catheter relative to the outer catheter;
wherein the bearing frame comprises a plurality of bearing bars arranged along a circumferential direction, each bearing bar is configured as a spiral bar, and proximal and distal ends of each bearing bar deflect a predetermined angle in the circumferential direction.

20. The ablation device according to claim 1, wherein the bearing bar is provided with an insulating layer at positions without the ablation members, and the bearing bar conducts electrical currents to the ablation members to ablate tissue during use.

* * * * *